(12) United States Patent
Woldegergis

(10) Patent No.: US 10,537,412 B2
(45) Date of Patent: Jan. 21, 2020

(54) DEVICE AND METHOD FOR HOLDING PROSTHETIC TEETH

(71) Applicant: Kulzer GmbH, Hanau (DE)

(72) Inventor: Yohannes Woldegergis, Hanau (DE)

(73) Assignee: Kulzer GmbH, Hanau (DE)

(*) Notice: Subject to any disclaimer, the term of this patent is extended or adjusted under 35 U.S.C. 154(b) by 124 days.

(21) Appl. No.: 15/561,863

(22) PCT Filed: Apr. 19, 2016

(86) PCT No.: PCT/EP2016/058630
§ 371 (c)(1),
(2) Date: Sep. 26, 2017

(87) PCT Pub. No.: WO2016/169921
PCT Pub. Date: Oct. 27, 2016

(65) Prior Publication Data
US 2018/0110599 A1    Apr. 26, 2018

(30) Foreign Application Priority Data

Apr. 23, 2015  (DE) .................. 10 2015 106 270

(51) Int. Cl.
*B25B 1/00* (2006.01)
*A61C 13/12* (2006.01)
(Continued)

(52) U.S. Cl.
CPC ............... *A61C 13/12* (2013.01); *A61C 5/77* (2017.02); *A61C 13/0004* (2013.01);
(Continued)

(58) Field of Classification Search
CPC .... B25B 1/00; B25B 1/02; B25B 1/20; B25B 5/00; B25B 5/16
See application file for complete search history.

(56) References Cited

U.S. PATENT DOCUMENTS 4,371,339 A * 2/1983 Zeiser .................... A61C 9/002
433/29
4,412,822 A * 11/1983 Blechner ............. A61C 11/001
433/54

(Continued)

FOREIGN PATENT DOCUMENTS

DE    102009056752 A1    6/2011
DE    102011101678 A1    11/2012
(Continued)

OTHER PUBLICATIONS

Office Action in German Application No. 10 2015 106 270.4 dated Mar. 10, 2016, 6 pages.
(Continued)

*Primary Examiner* — Lee D Wilson
(74) *Attorney, Agent, or Firm* — Marshall, Gerstein & Borun LLP

(57) ABSTRACT

The invention relates to a device for holding prosthetic teeth (2), the device comprising a negative form (1) and at least one clamping unit (6), wherein in the negative form (1), recesses (4) for holding coronal sides (12) of the prosthetic teeth (2) are provided, wherein the recesses (4) are formed in such a manner that the prosthetic teeth (2) can be inserted in an unequivocally position and orientation into the recesses (4), wherein the at least one clamping unit (6) is affixable or is affixed to the negative form (1) with a connecting means (10), and wherein the at least one clamping unit (6) has at least one elastic holding means (8), wherein with the at least one elastic holding means (8), an elastic force is exercisable or is exerted from at least two different directions onto the prosthetic teeth (2) inserted into the negative form (1), while the at least one clamping unit (6) is affixed to the negative form (1), so that the prosthetic teeth (2) are affixed in the device. The invention also relates to a method for affixing, and preferably processing, pros- (Continued)

thetic teeth (2) and a set for implementing such a method, having several prefabricated prosthetic teeth (2) and at least one such device.

34 Claims, 8 Drawing Sheets

(51) Int. Cl.
| | | |
|---|---|---|
| *A61C 13/36* | (2006.01) | |
| *B25B 1/06* | (2006.01) | |
| *B25B 1/20* | (2006.01) | |
| *B25B 1/24* | (2006.01) | |
| *B25B 5/06* | (2006.01) | |
| *B25B 5/14* | (2006.01) | |
| *B25B 5/16* | (2006.01) | |
| *A61C 5/77* | (2017.01) | |
| *A61C 13/00* | (2006.01) | |

(52) U.S. Cl.
CPC ............ *A61C 13/1016* (2013.01); *B25B 1/06* (2013.01); *B25B 1/20* (2013.01); *B25B 1/241* (2013.01); *B25B 5/06* (2013.01); *B25B 5/14* (2013.01); *B25B 5/163* (2013.01); *A61C 13/0022* (2013.01)

(56) References Cited

U.S. PATENT DOCUMENTS

| | | | | |
|---|---|---|---|---|
| 4,448,406 A | * | 5/1984 | Hallberg | ................. B25B 1/103 269/224 |
| 4,572,564 A | * | 2/1986 | Cipolla | ................. B25B 1/2421 269/266 |
| 5,145,157 A | * | 9/1992 | Polk | ........................ B25B 1/241 269/210 |
| 8,376,340 B2 | * | 2/2013 | Sandmeier | ............... B23Q 3/12 269/101 |
| 9,295,534 B2 | | 3/2016 | Ruppert et al. | |
| 10,390,914 B2 | * | 8/2019 | Savic | ................. A61C 13/0001 |
| 2011/0291342 A1 | * | 12/2011 | Gindy | ................... B25B 1/2421 269/266 |
| 2014/0087327 A1 | | 3/2014 | Noack | |
| 2015/0066181 A1 | | 3/2015 | Beyer et al. | |
| 2016/0278893 A1 | | 9/2016 | Savic et al. | |
| 2017/0035538 A1 | | 2/2017 | Savic et al. | |
| 2018/0110599 A1 | * | 4/2018 | Woldegergis | ............. B25B 1/06 |

FOREIGN PATENT DOCUMENTS

| | | | | |
|---|---|---|---|---|
| DE | 102012007706 A1 | 10/2013 | | |
| DE | 102013112747 A1 | 5/2015 | | |
| DE | 102014105190 A1 | 10/2015 | | |
| WO | WO-2011/066895 A1 | 6/2011 | | |
| WO | WO-2013/0124452 A1 | 8/2013 | | |
| WO | WO-2013124452 A1 | * | 8/2013 | ........... A61C 9/0053 |

OTHER PUBLICATIONS

Search Report in International Application No. PCT/EP2016/058630 dated Jul. 14, 2016.

International Preliminary Report on Patentability in International Application No. PCT/EP2016/058630 dated Oct. 24, 2017, 6 pages.

* cited by examiner

DEVICE AND METHOD FOR HOLDING PROSTHETIC TEETH

BACKGROUND OF THE INVENTION

Field of the Invention

The invention relates to a device for holding prosthetic teeth and a method for positioning and processing prosthetic teeth.

The invention also relates to a set for implementing such a method with such a device.

The invention thus relates to the production and preparation of prefabricated prosthetic teeth for further processing for partial and total synthetic dentures, which are produced mechanically using the CAM method (CAM—Computer-Aided Manufacturing), and which are designed using computers with the CAD method (CAD—Computer-Aided Design). The prosthetic teeth can be provided as a semi-finished product for the partial or total production of dental plastics using the CAM method.

Related Technology

Currently the most common method is the analog production of prosthetic teeth. Here, the prosthetic teeth are manually and individually arranged on a wax base. This wax prosthesis is then embedded in a cuvette with plaster as a next step, before the wax base is washed out with hot water after the plaster has hardened, creating a hollow space for the dental plastic. The prosthetic teeth remain in the plaster. A corresponding plaster is injected or "plugged" into the hollow space and after the plastic has hardened, the prosthesis or finished prosthetic tooth is obtained.

When arranging prefabricated prosthetic teeth, said teeth are adapted to the respective mouth situation of the patient by the dental technician and ground. Initial methods are already available, such as those methods known from DE 10 2009 056 752 A1 or WO 2013 124 452 A1, in which the partial or total prosthesis is digitally arranged and produced using the CAD-CAM method.

The disadvantage of these methods is the positioning of the prosthetic teeth in a denture base plate. Generally, a precisely fitted mold is prefabricated for this purpose in a denture base plate, in order to then glue in the prefabricated prosthetic teeth. However, this only functions when sufficient space is available. In most cases, the prosthetic teeth must be ground for reasons of space. Prefabricated prosthetic teeth must usually at least be basally processed during the creation of prosthetic products.

With manual implementation, processing is completed individually for each prosthetic tooth by the processor. In this case, however, it no longer fits into the pre-produced mold in the denture plate.

DE 10 2011 101 678 A1 recommends that the crown area of a prosthetic tooth be embedded in a carrier layer, before then processing the prosthetic tooth. This affixing of the prosthetic teeth is achieved either using wax or other masses that can be melted or hardened. As a result, a fixed, precise connection is achieved, with a defined position of the prosthetic teeth at the same time. The disadvantage here is that the prosthetic tooth must be exposed in some areas in order to process the embedded crown area. The disadvantages of the method also lie in the complex production of the corpuses. These must be produced individually or in groups by inserting the finished prosthetic teeth into a holder, arranged an outer frame and then pouring out with a connecting medium (e.g. wax). As a result, the pouring in of the prosthetic teeth with the mass that forms the carrier layer requires a great deal of manual skill.

The carrier layer must harden before the prosthetic tooth can be processed, since in particular when automated CAM mills are used, considerable forces can occur. The positioning precision of the method also suffers from potential deformations of the not yet fully hardened carrier layer, so that in extreme cases, the adjacent prosthetic tooth is not milled out precisely enough and must therefore be disposed of. Further, such a carrier layer can usually only be removed fully from the prosthetic tooth again with a certain amount of effort involved. After use, the residues of the removed carrier layer must be disposed of.

SUMMARY

The object of the invention is therefore to overcome the disadvantages of the prior art. In particular, a device and a method are to be provided with which the most simple, complete and low-cost processing of the prosthetic teeth is possible. Here, the fewest possible post-processing steps should be necessary. As many of the necessary parts as possible should be re-usable in order to enable serial processing.

The objects of the invention are attained by a device for holding prosthetic teeth, the device comprising a negative form and at least one clamping unit, wherein recesses for holding coronal sides of the prosthetic teeth are provided in the negative form, wherein the recesses are formed in such a manner that the prosthetic teeth can be inserted in an unequivocally position and orientation into the recesses, wherein the at least one clamping unit is affixable or is affixed to the negative form with a connecting means, and wherein the at least one clamping unit has at least one elastic holding means, wherein with the at least one elastic holding means, an elastic force is exercisable or is exerted from at least two different directions onto the prosthetic teeth inserted into the negative form, while the at least one clamping unit is affixed to the negative form, so that the prosthetic teeth are affixed in the device.

According to the invention, the connecting means is preferably a part of the device, wherein in a particularly preferred manner, the connecting means are connected to the negative form and/or the clamping unit. According to the invention, the device therefore also has the connecting means alongside the negative form and the clamping unit.

The at least one holding means can be elastic in itself, e.g. a rubber block or a synthetic foam or the at least one holding means can exert an elastic force through deformation, such as a steel spring or a metal clasp or an elastic synthetic material.

The clamping unit and the holding means can be produced using the 3D printing method. Through a structure of the holding means as a grid or through a pore structure, it is possible that the holding means has a different elasticity to the rest of the clamping unit, which can for example be printed solidly from the same material.

With the invention, it is also recommended that the at least one clamping unit is affixed on the side of the negative form in which the recesses are arranged.

As a result, it can be achieved that the elastic force has a vector component which presses the prosthetic teeth into the recesses of the negative form.

Additionally, it can be provided according to the invention that the recesses form negatives of the coronal ends of the prosthetic teeth.

As a result, a particularly good fitting form is achieved and the prosthetic teeth are well defined in their position and alignment in the negative form.

With a further development of the present invention, it is recommended that the negative form has an even surface, in which the recesses are arranged, wherein preferably, the negative form has a standing side or arrangement area opposite the even surface, wherein in a particularly preferred manner, the negative form is a plate.

As a result, processing of the prosthetic teeth affixed in the device is simplified.

At the same time, the use of the device when inserting the prosthetic teeth is made easier for the user.

It can also be provided that the device has several prosthetic teeth, wherein the prosthetic teeth are inserted into the recesses and affixed on the negative form with the at least one clamping unit.

When the prosthetic teeth are already affixed in the desired position and alignment in the device, the work required to insert them into the device is no longer required, and at the same time, potential faulty applications are also excluded.

Further, it can be provided that the connecting means comprises at least one pin, at least one bore hole, at least one plug-in connection, at least one groove, at least one tongue, at least one bracket, at least one clamp, at least one threaded rod, at least one screw, at least one threaded bore, at least one latching means, at least one push button or at least one adhesive, or a combination of these means, with which the at least one clamping unit is affixable or is affixed to the negative form.

With these connecting means, a reliable, detachable connection of the clamping unit to the negative form can be achieved. When an adhesive is used, it is important that the adhesive can be detached without great effort and under conditions which do no damage the prosthetic teeth. For example, a wax can be used as an adhesive, which becomes fluid at temperatures between 60° C. and 110° C.

Preferred embodiments of the device according to the invention can be characterized by the fact that the negative form is a single part.

As a result, the effort involved in the use of the negative form can be avoided.

Further, it can be provided that the at least one clamping unit is multi-part, and on the parts of the at least one clamping unit, fastening means are provided via which the parts are to be affixed to each other.

As a result, the arrangement of the at least one clamping unit to the prosthetic teeth can be facilitated. Alternatively, a single-part clamping unit can also be laid over the prosthetic teeth from the direction of the base of the prosthetic teeth.

Preferably, it can also be provided that the at least one elastic holding means consists of a non-plastically deformable material, preferably of a material with an elasticity modulus of at least 0.2 GPa, particularly preferred, 0.2 GPa to 6 GPa.

In this case, the material is preferably a synthetic material. With these materials or with such materials with these elasticity moduli, an elastic force can be exerted on the prosthetic teeth without the holding means being pressed into the prosthetic teeth and damaging them. At the same time, the elastic force for affixing is sufficient in order to be able to absorb the forces arising during processing of the prosthetic teeth, without the position and the location of the prosthetic teeth in the device changing.

According to one preferred embodiment of the invention, it can be provided that the at least one elastic holding means is at least one metal strip, in particular a strip made of spring steel, wherein preferably, synthetic coatings are provided on the surfaces of the holding means pointing towards the prosthetic teeth.

As a result, the clamping unit can be particularly simply and reversibly affixed to the prosthetic teeth. The metal strips are preferably formed as braces. The production of a clamping unit with such holding means is possible in a particularly simple and low-cost manner.

Preferably, it can also be provided that the basal ends of the prosthetic teeth affixed in the device protrude from the composite device.

In this way, it is achieved that the basal ends of the prosthetic teeth can later be well processed while they are affixed in the device, so that the device can for example be used as a holder for a mill.

Additionally, it can be provided that the recesses are of such a depth that they extend up to a maximum of the beginning of the undercut zones of the prosthetic teeth.

Through this measure, it can be achieved that the prosthetic teeth already sit sufficiently stably in the recesses after insertion into the negative form that the clamping unit can be affixed to the negative form without a great effort, without the position and location of the prosthetic teeth being confused.

Additionally, it can be provided that the recesses are of such a depth that they hold at least 10% of the height of the prosthetic teeth, preferably that they hold at least 25% of the height of the prosthetic teeth.

The height of the prosthetic teeth is the length of the prosthetic teeth from the basal end of the prosthetic teeth through to the coronal end of the prosthetic teeth.

Further, it can be provided that in each recess, at least one through-connection is provided, through which an underpressure is producible in the recess.

The at least one through-connection can for example be a through-bore, which extends from the recess through to a surface of the negative form outside the recess and which can be connected or is connected to an underpressure source. With this measure, the prosthetic teeth can be suctioned into the recesses, and as a result, be affixed in the recesses or on the negative form. Additionally, with the correct form of the recesses, the prosthetic teeth are suctioned into the correct position and alignment. The effect is therefore particularly strong when the recesses are negatives of the coronal sides of the prosthetic teeth. As soon as the prosthetic teeth are affixed with the at least one clamping unit, the prosthetic teeth must no longer be suctioned into the recesses with the vacuum or underpressure. Preferably, therefore, the connection to the underpressure source is released after the clamping unit has been affixed to the negative form.

With a further embodiment of the invention, it is recommended that the at least one holding means of the at least one clamping unit lies on the tooth necks of the prosthetic teeth.

As a result, it is ensured that the basal sides of the prosthetic teeth are exposed for processing. Preferably, the elastic force acts in a punctiform manner from at least three directions in a punctiform manner on the tooth neck of each prosthetic tooth, or the elastic force acts over at least two areas or lines from at least two directions on the tooth neck of each prosthetic tooth. As a result, a sufficiently stable affixation of the prosthetic teeth in the device is achieved.

Preferred devices according to the invention can be characterized by the fact that the sum of the elastic forces of the at least one holding means applied onto the prosthetic teeth presses the prosthetic teeth in the direction of the recesses of the negative form.

The at least one holding means applied means the at least one holding means applied onto the prosthetic teeth which are inserted into the negative form. As a result, a secure seat of the prosthetic teeth in the device is guaranteed, in particular when the recesses are negatives of the coronal sides of the prosthetic teeth.

The objects that form the basis of the present invention are also attained by means of a method for affixing, and preferably for processing, prosthetic teeth, in particular with a device according to the invention, having the following method steps:

A) several prosthetic teeth are inserted into recesses of a negative form,

B) subsequently, at least one clamping unit is applied to the inserted prosthetic teeth, wherein at least one elastic holding means of the at least one clamping unit is applied on at least two directions on the tooth necks of the prosthetic teeth, and C) affixing of the at least one clamping unit on the negative form, so that an elastic force of the at least one elastic holding means acts on the prosthetic teeth from at least two directions, wherein the prosthetic teeth are affixed against the negative form as a result.

The tooth neck of a prosthetic tooth is the circumference of the prosthetic tooth between the coronal end and the basal end.

Steps B) and C) can be conducted simultaneously.

Here, it can be provided that when the at least one clamping unit is applied, the at least one holding means enclose the prosthetic teeth on their tooth necks at least in sections, wherein the inner areas of the at least one holding means fit at least in sections in an engaging manner to sections of the outer areas of the prosthetic teeth.

As a result, at particularly stable affixation of the prosthetic teeth in the device is achieved, and at the same time, the elastic force for holding is distributed on the surface of the tooth necks in such a manner that no mechanical impairment, such as a pressing in of the surface or another plastic deformation of the prosthetic teeth, and also of the at least one holding means, is to be feared.

Further, it can be provided that the at least one clamping unit is applied to the prosthetic teeth in such a manner that the basal ends of the prosthetic teeth protrude.

As a result, it is ensured that the prosthetic teeth can be processed basally.

Further, it can be provided that the at least one clamping unit and the negative form with the prosthetic teeth affixed in it are affixed in a defined position in a holder of a CAM device for removing material of the prosthetic teeth with a CAM method, and at least one basal end of at least one prosthetic tooth is processed in a computer-controlled manner using the CAM device, wherein the CAM device is preferably a computer-controlled milling machine, particularly preferred, a computer-controlled four-axis mill or five-axis mill.

Thus, the method is completed with regard to the basal processing of the prosthetic teeth. This step exploits the advantages offered by a device according to the invention and the method for positioning according to the invention for automated methods in which the exact positioning according to the invention has a particularly advantageous impact.

It is also recommended that the outer forms of all pre-fabricated prosthetic teeth used are present as a first data set, and a second data set defines the precise positions of all affixed pre-fabricated prosthetic teeth in the negative form, wherein a subsequent processing at least of one prosthetic tooth on the basis of the first and second data set is conducted, preferably a subsequent processing using a CAD/CAM method is conducted on the basis of the first and second data set.

As a result, the advantages of affixation for fully automated post-processing methods are made accessible, for which they are particularly well suited. Only through the claimed affixation is a simple, low-cost provision of the prosthetic teeth namely possible to a high degree of precision and position accuracy.

With one further development, it is recommended that all pre-fabricated prosthetic teeth can only be inserted in one specified position and orientation respectively into the negative form, and can be affixed with the at least one clamping unit.

As a result, it is ensured that an unequivocally position and orientation is provided for post-processing, without the position and the orientation having to be checked again. According to the invention, the orientation is also known as the position or alignment of the prosthetic teeth. The position can preferably also be given by the natural arrangement and sequences of the prosthetic teeth, so that an intuitively correct arrangement of the prosthetic teeth is supported. It can also be provided that before inserting the prosthetic teeth into the negative form, a bonding agent is applied to the surface of the recesses and/or to the surface of the coronal sides of the prosthetic teeth.

As a result, a better hold of the prosthetic teeth in the recesses of the negative form can be achieved. The bonding agent must usually be removed again from the prosthetic teeth, however, if it does not evaporate by itself. For this reason, a suctioning of the prosthetic teeth into the recesses through at least one gas-permeable passage in every recess is preferred according to the invention.

The objects that form the basis of the present invention are also attained by means of a set for implementing a method according to the invention, comprising several pre-fabricated prosthetic teeth and at least one device according to the invention.

Here, it can be provided that the set additionally contains the first data set on the outer form of all pre-fabricated prosthetic teeth, and a second data set on the position of the pre-fabricated prosthetic teeth in the composite device, preferably on a data storage device.

The combination of the set with the data set renders the set more complete and easier to apply for the user. Additionally, as a result, a fully automated post-processing of the prosthetic teeth is facilitated.

The invention is based on the surprising finding that prosthetic teeth must be reversibly affixed to the negative form with the aid of elastic fastening means via a clamping unit to be fastened to the negative form in such a manner that the basal ends of the prosthetic teeth are freely accessible, so that the basal ends of the prosthetic teeth can be processed with a mill. The device, the method and the set are particularly suitable for use with the CAD/CAM method, particularly with CAM-controlled or computer-controlled mills. The post-processed prosthetic teeth can be removed free of residues by releasing the clamping unit following basal processing, and are immediately available for the treatment of a patient. The prosthetic teeth are quick and uncomplicated to affix. The clamping unit can without a problem be constructed in such a way that it is re-usable. Complex production of the holder, as is required with wax holders, is no longer necessary with the device according to the invention and the method according to the invention.

The device and the clamping unit are stable with regard to external influences such as heat or cold, and warping or deformations of the device, and thus position changes of the prosthetic teeth within the device, do not occur.

The major advantage of methods according to the invention lies in the very rapid and almost tool- and equipment-free implementation. As a result, no larger stock quantities need to be stored, and an order-related pre-fabrication is possible. Also, the cleaning required with wax using extraction or cleaning of the prosthetic teeth is no longer required.

The method is also highly efficient in relation to costs, since depending on the degree of grinding of the prosthetic teeth, the clamping unit and the negative form can be re-used.

The application of bonding agents can further improve the connection of the device to the prosthetic teeth. As an example of a bonding agent, poly vinyl alcohol can be used, which after evaporation of the solvents contained forms an adhesive bonding layer.

The invention can for example provide that the prosthetic teeth are provided affixed in the device, so that in the CAM method they can be directly mechanically basally ground and thus adapted to the individual patient situation.

In order to be able to implement this technical approach, the pre-fabricated prosthetic teeth must be positioned and affixed in a pre-defined position within the device that can be tensioned in the machine. The composite device can have different forms (cuboid, rectangular, round etc.) and is advantageously adapted to the holding mechanism of the respective CAM machine. For this purpose, it can be provided according to the invention that on the negative form and/or on the clamping unit, or on at least one part of the clamping unit, a holder is provided for affixing in the CAM machine. The pre-fabricated, ready-made prosthetic teeth are here preferably pressed by the clamping unit into the recesses of the negative form. The prosthetic teeth and the clamping unit are not damaged when the prosthetic teeth are removed, and can be re-used if necessary.

The prosthetic teeth are affixed via the negative form for holding the coronal ends and by the clamping unit. The clamping unit is positioned at the side on the prosthetic teeth, or on the surface running around on the side of the prosthetic teeth between the basal and coronal end of the prosthetic teeth, i.e. the tooth necks of the prosthetic teeth, and then with the negative form and, if the clamping unit is multi-part, the parts, is firmly bonded (for example through adhesion, screwing, click mechanism, retentions, groove and tongue or holding pins, or a combination of these). As a result, the prosthetic teeth are clamped or tensioned in a defined position and orientation. As an option, the positioning of the clamping unit against the negative form and/or the parts of the clamping unit against each other can be secured against each other with additional guides, dowels or similar.

The negative form and a large part of the clamping unit are preferably made of a form-stable material, such as an elastic synthetic material such as polyurethane methacrylate (PMMA) or polyurethane (PU) or other synthetic materials with filler material portions, or of metallic materials. The negative form is preferably produced using milling technology, but can however also be produced using injection molding or sintering.

BRIEF DESCRIPTION OF THE DRAWINGS

Exemplary embodiments of the invention will now be explained below with reference to eight schematically shown figures, although without thereby limiting the invention.

In the figures.

DETAILED DESCRIPTION

Figure 1:
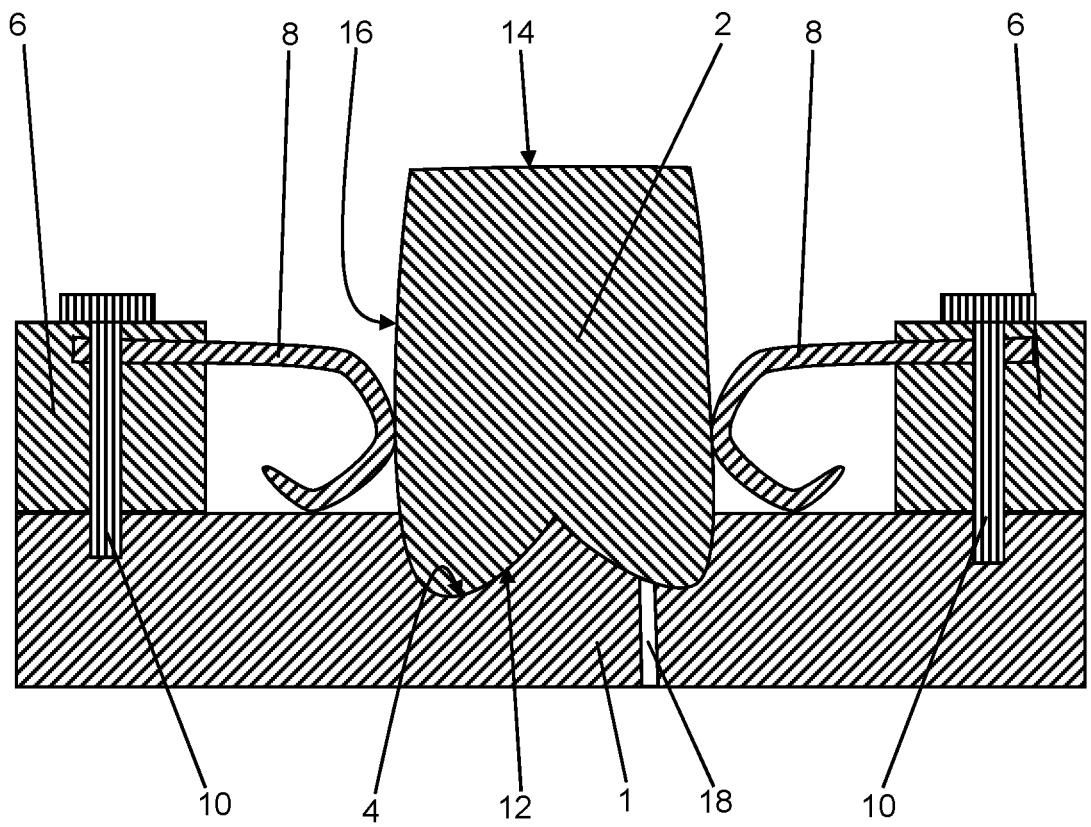
FIG. 1: shows a schematic profile view of a device according to the invention.

In the figures, the same reference numerals are also used for different designs for the same parts.

FIG. 1 shows a schematic profile view of a device according to the invention, wherein cut areas are shown shaded. The device has a negative form 1 on the floor side (in FIG. 1 below) in the form of a panel, in which several prosthetic teeth 2 (of which only one can be seen in the profile view shown in FIG. 1) are arranged. The prosthetic teeth 2 are inserted into matching recesses 4 in the negative form 1. The negative form 1 consists of a form-stable material, such as a not too soft material, for example brass or steel, but not lead, or of a hard synthetic material such as PMMA.

The prosthetic teeth 2 are held at the side by a clamping unit 6, which has several braces 8 made of spring steel, which are aligned in the direction of the prosthetic teeth 2 and are tensioned counter to the direction of the prosthetic teeth 2. Aside from the braces 8, the clamping unit 6 consists of a solid, hard synthetic material such as PMMA. On the surfaces of the braces 8 that point towards the prosthetic teeth 2, a synthetic coating is provided in order to avoid damage to the prosthetic teeth 2. With the aid of screws 10, the clamping unit 6 is affixed on the negative form 1. For this purpose, threaded bores are provided in the negative form 1, into which the screws 10 are screwed in. In addition, guide elements (not shown) can be provided which guarantee the correct positioning of the clamping unit 6 on the negative form 1. As guide elements, rails, grooves and tongues and/or holes and pins can be used, which are arranged on the negative form 1 and the clamping unit 6.

The prosthetic teeth 2 have a coronal side 12 (in FIG. 1 below), a basal side 14 (in FIG. 1 above) and a circumferential tooth neck 16 between the coronal side 12 and the basal side 14 of the prosthetic teeth 2.

The recesses 4 form a negative of the coronal sides 12 of the prosthetic teeth 2, so that the prosthetic teeth 2 can be inserted flush into the recesses 4 with the coronal side 12. In addition to an easy hold, the position of the prosthetic teeth 2 which differ from each other is clearly specified. In the recess 4, a bore 18 is provided, by means of which an underpressure can be generated in the recess 4, so that the prosthetic tooth 2 is suctioned into the recess 4 and held there until the clamping unit 6 is affixed on the negative form 1.

The braces 8 are positioned in the clamping unit 6 in such a manner that they are elastically formed by the prosthetic teeth 2. As a result, an elastic force is exerted on the prosthetic teeth 2, which affix the prosthetic teeth 2 on the negative form 4 and in the clamping unit 6. The position and alignment of the prosthetic teeth 2 is here specified by the unequivocal form of the recesses 4. The braces 8 here exert such an elastic force on the prosthetic teeth 2 that the prosthetic teeth 2 are pressed into the recesses 4. The braces 8 can for example be formed from metal strips made of spring steel, which are anchored or poured or inserted in the synthetic body of the clamping unit 6.

As soon as the prosthetic teeth 2 are affixed with the clamping unit 6, the underpressure on the bore 18 can be removed, i.e. the underpressure source can be disconnected. The device with the affixed prosthetic teeth 2 is then inserted into a computer-controlled milling machine (not shown) and the prosthetic teeth 2 are processed on the basal side 14 with the mill. With the known form of the device and with known pre-fabricated prosthetic teeth 2, their form, position and location can be used as a data set, on the basis of which it is calculated using a CAM program in the computer according to known methods at which points basal material must be removed from the prosthetic teeth 2. The stabilization and affixation of the prosthetic teeth 2 with the device is so stable that a basal processing of the prosthetic teeth 2 with a mill is possible without the position and location of the prosthetic teeth 2 being changed in the device as a result of the mechanical load.

Following processing of the prosthetic teeth 2, these can be simply removed from the negative form 1 by releasing the clamping unit 6 from the negative form 1, in other words, by removing the screws 10, and glued into a prosthetic base (not shown) for producing a dental prosthesis.

Figure 2:
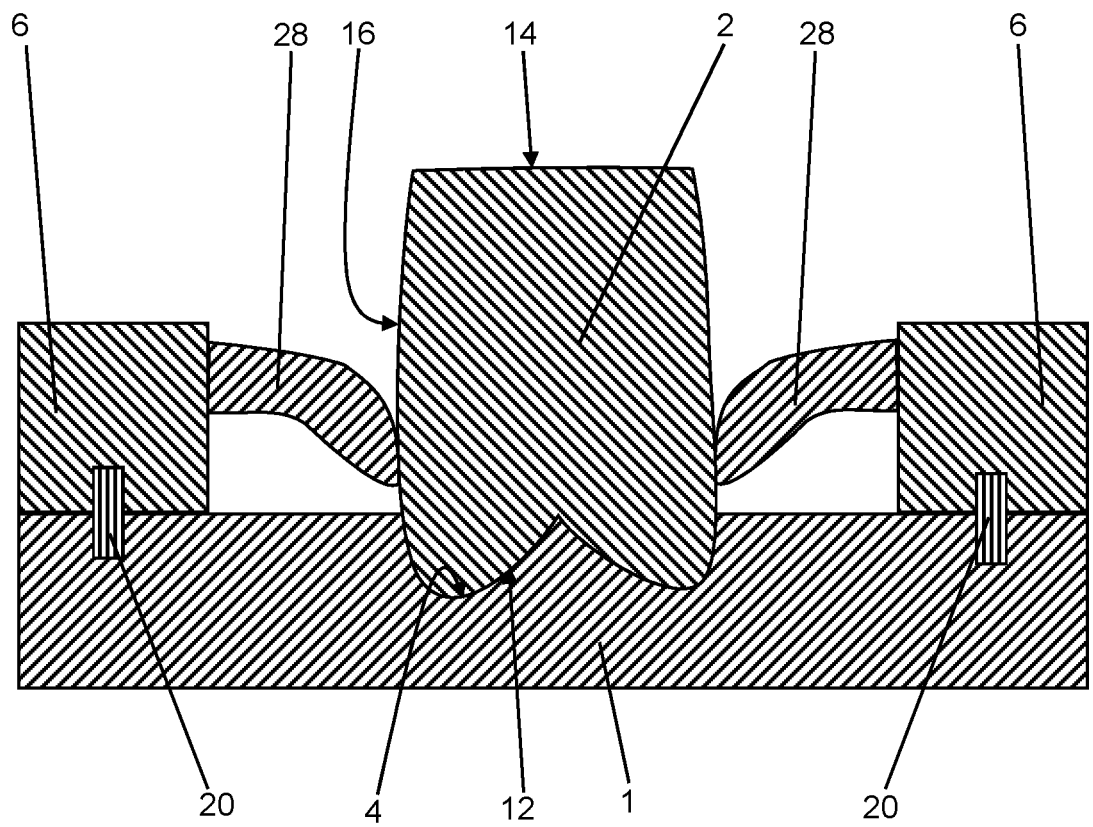
FIG. 2: shows a schematic profile view of an alternative device according to the invention.

FIG. 2 shows a schematic profile view of an alternative device according to the invention, wherein cut areas are shown shaded. The device has a negative form 1 on the floor side (in FIG. 2 below) in the form of a panel, in which several prosthetic teeth 2 (of which only one can be seen in the profile view shown in FIG. 2) are arranged. The prosthetic teeth 2 are inserted into matching recesses 4 in the negative form 1. The negative form 1 consists of a form-stable material, such as a not too soft material, for example brass or steel, but not lead, or of a hard synthetic material such as PMMA.

The prosthetic teeth 2 are held at the side by a clamping unit 6, which has several synthetic braces 28 made of an elastic, soft synthetic material, which are aligned in the direction of the prosthetic teeth 2 and are tensioned or compressed counter to the direction of the prosthetic teeth 2. The clamping unit 6 consists of a solid, hard synthetic material such as PMMA. With the aid of pins 20, the clamping unit 6 is affixed on the negative form 1. For this purpose, bores are provided in the negative form 1 and the clamping unit 6, into which the pins 20 are inserted. In addition, guide elements (not shown) can be provided which guarantee the correct positioning of the clamping unit 6 on the negative form 1. As guide elements, rails, grooves and tongues and/or holes and additional pins can be used, which are arranged on the negative form 1 and the clamping unit 6.

The prosthetic teeth 2 have a coronal side 12 (in FIG. 1 below), a basal side 14 (in FIG. 1 above) and a circumferential tooth neck 16 between the coronal side 12 and the basal side 14 of the prosthetic teeth 2.

The recesses 4 form a negative of the coronal sides 12 of the prosthetic teeth 2, so that the prosthetic teeth 2 can be inserted flush into the recesses 4 with the coronal side 12. In addition to an easy hold, the position of the prosthetic teeth 2 which differ from each other is clearly specified. In the recess 4, a bore (not shown) or a plurality of passages (not shown) are provided, by means of which an underpressure can be generated in the recess 4, so that the prosthetic tooth 2 is suctioned into the recess 4 and held there until the clamping unit 6 is affixed on the negative form 1. Alternatively, the negative form 1 can also be porous throughout between the recesses 4 and the underside, so that an underpressure on the floor side has an impact through to the recesses 4.

The synthetic braces 28 are positioned in the clamping unit 6 in such a manner that they are elastically formed by the prosthetic teeth 2. As a result, an elastic force is exerted on the prosthetic teeth 2, which affix the prosthetic teeth 2 on the negative form 4 and in the clamping unit 6. The position and alignment of the prosthetic teeth 2 is here specified by the unequivocal form of the recesses 4. The synthetic braces 28 here exert such an elastic force on the prosthetic teeth 2 that the prosthetic teeth 2 are pressed into the recesses 4. The synthetic braces 28 can for example consist of a rubber elastic synthetic material and be anchored, glued, poured or inserted in the harder synthetic body of the clamping unit 6.

The clamping unit 6 and the synthetic braces 28 can be produced using the 3D printing method, for example. The clamping unit 6 and the synthetic braces 28 can here also be constructed from the same material, wherein the clamping unit 6 can be solid and the synthetic braces 28 can be printed with a grid structure or slightly porous, so that the synthetic braces 28 become more elastic as a result than the clamping unit 6.

As soon as the prosthetic teeth 2 are affixed with the clamping unit 6, the underpressure on the bore or the passages on the lower side of the negative form 1 can if necessary be removed, i.e. the underpressure source can be disconnected. The device with the affixed prosthetic teeth 2 is then inserted into a computer-controlled milling machine (not shown) and the prosthetic teeth 2 are processed on the basal side 14 with the mill. With the known form of the device and with known pre-fabricated prosthetic teeth 2, their form, position and location can be used as a data set, on the basis of which it is calculated using a CAM program in the computer according to known methods at which points basal material must be removed from the prosthetic teeth 2. The stabilization and affixation of the prosthetic teeth 2 with the device is so stable that a basal processing of the prosthetic teeth 2 with a mill is possible without the position and location of the prosthetic teeth 2 being changed in the device as a result of the mechanical load.

Following processing of the prosthetic teeth 2, these can be removed from the negative form 1 by releasing the clamping unit 6 from the negative form 1, in other words, by simply pulling out the clamping unit 6 from the pins 20, and glued into a prosthetic base (not shown) for producing a dental prosthesis.

Figure 3:
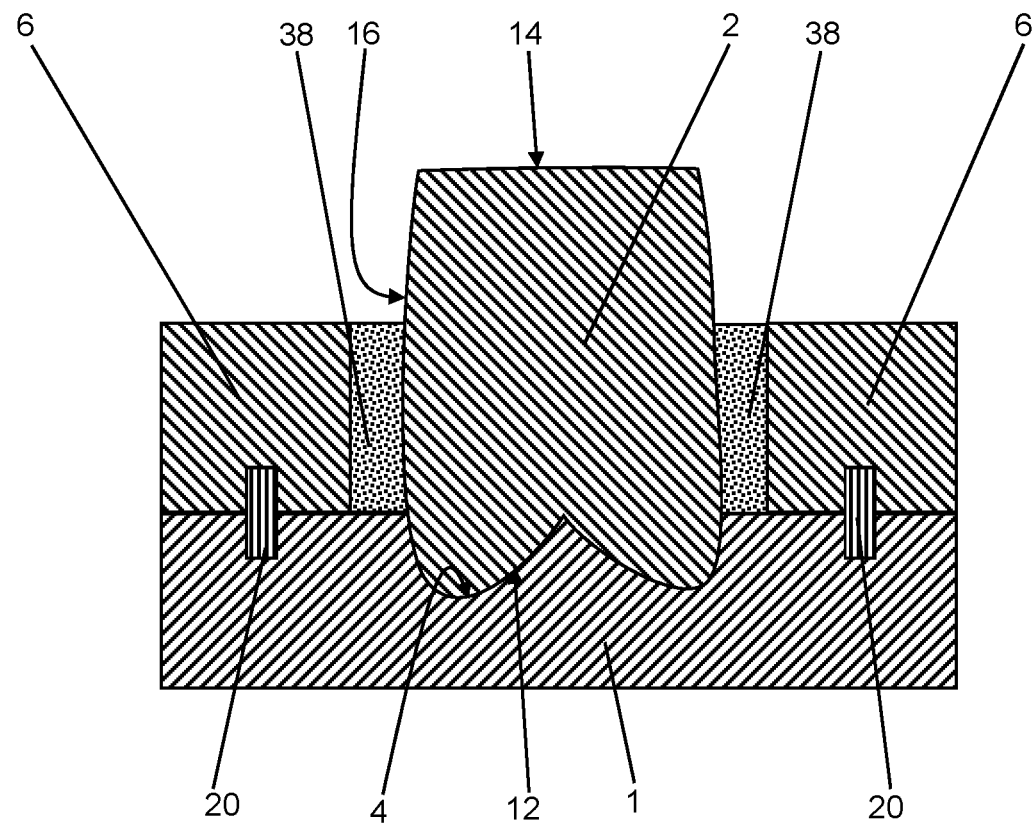
FIG. 3: shows a schematic profile view of a further alternative device according to the invention.

FIG. 3 shows a schematic profile view of a further alternative device according to the invention, wherein cut areas are shown shaded. The device has a negative form 1 on the floor side (in FIG. 3 below) in the form of a panel, in which several prosthetic teeth 2 (of which only one can be seen in the profile view shown in FIG. 3) are arranged. The prosthetic teeth 2 are inserted into matching recesses 4 in the negative form 1. The negative form 1 consists of a form-stable material, such as a not too soft material, for example brass or steel, but not lead, or of a hard synthetic material such as PMMA.

The prosthetic teeth 2 are held at the side by a clamping unit 6, which has several soft synthetic inserts 38 made of an elastic, soft synthetic material, such as a porous or foam-like sponge, and which are aligned in the direction of the prosthetic teeth 2 and are tensioned or compressed counter to the direction of the prosthetic teeth 2. The clamping unit 6 consists of a solid, hard synthetic material such as PMMA. With the aid of pins 20, the clamping unit 6 is affixed on the negative form 1. For this purpose, bores are provided in the negative form 1, into which the pins 20 affixed on the clamping unit 6 are inserted. In addition, guide elements (not shown) can be provided which guarantee the correct positioning of the clamping unit 6 on the negative form 1. As guide elements, rails, grooves and tongues and/or holes and additional pins can be used, which are arranged on the negative form 1 and the clamping unit 6.

The prosthetic teeth 2 have a coronal side 12 (in FIG. 1 below), a basal side 14 (in FIG. 1 above) and a circumferential tooth neck 16 between the coronal side 12 and the basal side 14 of the prosthetic teeth 2.

The recesses 4 form a negative of the coronal sides 12 of the prosthetic teeth 2, so that the prosthetic teeth 2 can be inserted flush into the recesses 4 with the coronal side 12. In addition to an easy hold, the position of the prosthetic teeth 2 which differ from each other is clearly specified. In the recess 4, a bore (not shown) or a plurality of passages (not shown) are provided, by means of which an underpressure can be generated in the recess 4, so that the prosthetic tooth 2 is suctioned into the recess 4 and held there until the clamping unit 6 is affixed on the negative form 1. Alternatively, the negative form 1 can also be porous throughout between the recesses 4 and the underside, so that an underpressure on the floor side has an impact through to the recesses 4.

The synthetic inserts 38 are positioned in the clamping unit 6 in such a manner that they are elastically formed by the prosthetic teeth 2. As a result, an elastic force is exerted on the prosthetic teeth 2, which affix the prosthetic teeth 2 on the negative form 4 and in the clamping unit 6. The position and alignment of the prosthetic teeth 2 is here specified by the unequivocal form of the recesses 4. The synthetic inserts 38 can be harder above (in FIG. 3 above) than below, so that they exert such an elastic force onto the prosthetic teeth 2 that the prosthetic teeth 2 are pressed into the recesses 4. For this purpose, the synthetic insert 38 can also be thinner above than below. The synthetic inserts 38 can for example consist of a rubber elastic synthetic material or a foam rubber, and be glued in the harder synthetic body of the clamping unit 6.

The clamping unit 6 and the synthetic insert 38 can be produced using the 3D printing method, for example. The clamping unit 6 and the synthetic insert 38 can here also be constructed from the same material, wherein the clamping unit 6 can be solid and the synthetic insert 38 can be printed with a grid structure, so that the synthetic insert 38 becomes more elastic as a result than the clamping unit 6.

In order to achieve a higher clamping force of the synthetic inserts 38, on the outside on the clamping unit 6 (in FIG. 3, to the right and left of the clamping unit 6) a bracket or clamp (not shown) can be arranged, with which the clamping unit 6 is pressed together. For this purpose, the left-hand and right-hand part of the clamping unit 6 can be movably connected on rails with the negative form 1, instead of through the pins 20. The bracket or clamp can here additionally be used in order to affix the clamping unit 6 on the negative form 1.

As soon as the prosthetic teeth 2 are affixed with the clamping unit 6, the underpressure on the bore or the passages on the lower side of the negative form 1 can if necessary be removed, i.e. the underpressure source can be disconnected. The device with the affixed prosthetic teeth 2 is then inserted into a computer-controlled milling machine (not shown) and the prosthetic teeth 2 are processed on the basal side 14 with the mill. With the known form of the device and with known pre-fabricated prosthetic teeth 2, their form, position and location can be used as a data set, on the basis of which it is calculated using a CAM program in the computer according to known methods at which points basal material must be removed from the prosthetic teeth 2. The stabilization and affixation of the prosthetic teeth 2 with the device is so stable that a basal processing of the prosthetic teeth 2 with a mill is possible without the position and location of the prosthetic teeth 2 being changed in the device as a result of the mechanical load.

Following processing of the prosthetic teeth 2, these can be removed from the negative form 1 by releasing the clamping unit 6 from the negative form 1, in other words, by simply pulling out the clamping unit 6 from the pins 20, and glued into a prosthetic base (not shown) for producing a dental prosthesis.

Figure 4:
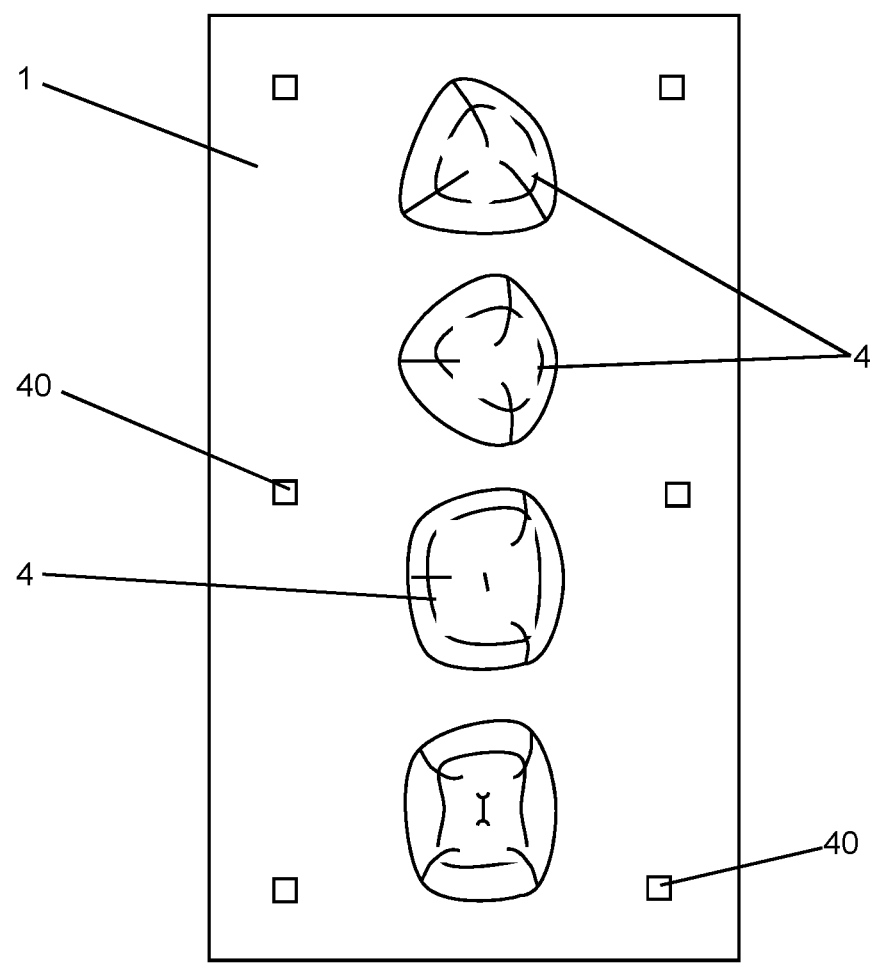
FIG. 4: shows a schematic profile view of a negative form of a device according to the invention.

FIG. 4 shows a schematic view onto a negative form 1 of a device according to the invention for holding prosthetic teeth, and for implementing the method according to the invention. The sequence of exemplary method steps according to the invention is shown in FIGS. 4 to 7.

The negative form 1 can for example consist of a simple, hard synthetic material or of metal such as steel or brass. In the negative form, four recesses 4 for positioning prosthetic teeth 2 are shown (not shown in FIG. 4, but shown in FIGS. 5 to 7). The recesses 4 are a negative of the outer form of the four coronal ends of prosthetic teeth 2, so that the prosthetic teeth 2 can and must be inserted clearly and correctly oriented into the recesses 4 on the coronal side. As an alternative to the four recesses 4 shown, preferably, also additional and further different recesses 4 can be provided for different prosthetic teeth 2 of different tooth types. According to the invention, preferably, the negative form 1 has twenty-eight recesses 4, of such a type that a complete dentition with prosthetic teeth 2 for a complete set of teeth can be inserted into the negative form 1. Next, with the embodiment shown in FIG. 4, four different prosthetic teeth 2 are inserted into the recesses 4.

Figure 5:
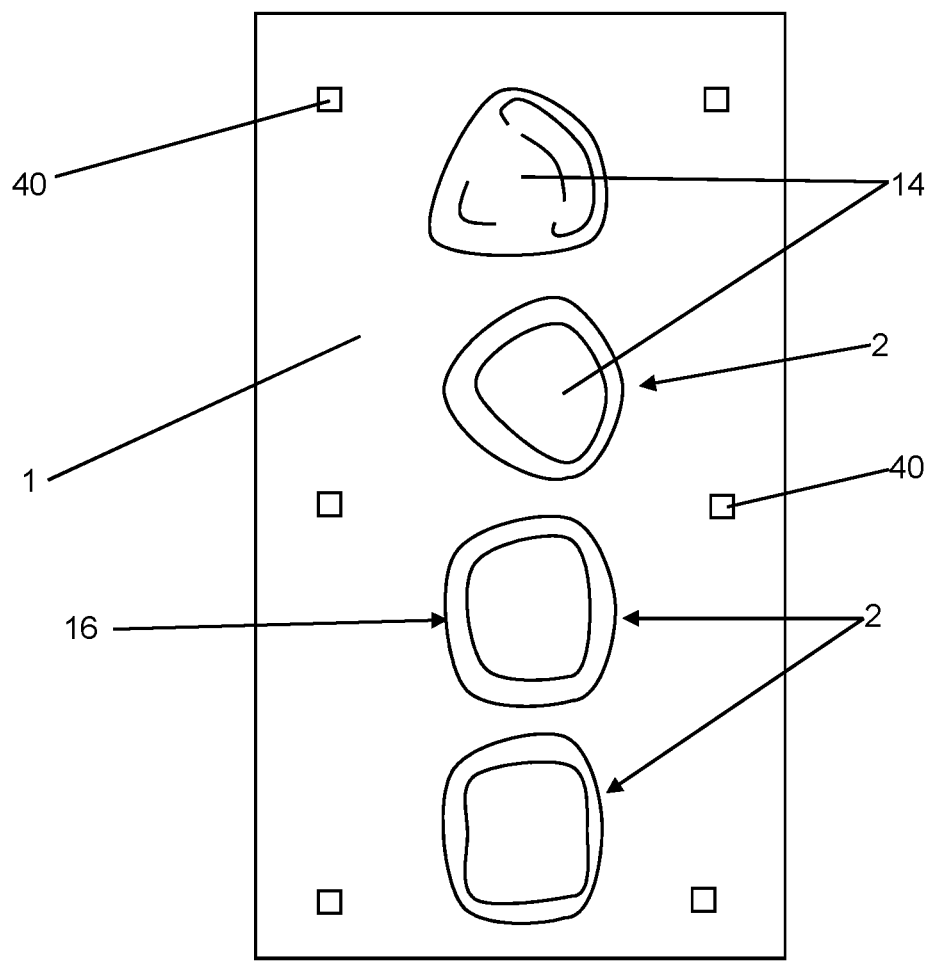
FIG. 5: shows a schematic top view onto the negative form shown in FIG. 4, with four inserted prosthetic teeth.

FIG. 5 shows a schematic top view onto the negative form 1 of a device according to the invention, with four inserted prosthetic teeth 2. The prosthetic teeth 2 can be inserted into the recesses 4 only in one certain position and one certain orientation. The prosthetic teeth 2 are inserted into matching recesses 4 in the negative form 1. However, it can also be provided that the prosthetic teeth 2 are adhered in the recesses 4 with a bonding agent, or through a suitable form of the recesses 4 are held in a light press fit in the recesses 4, or are suctioned into the recesses 4 by an underpressure as shown with the example according to FIG. 1. The basal sides 14 of the prosthetic teeth 2 are exposed with this arrangement. For this purpose, the prosthetic teeth 2 have been inserted with the coronal side 12 into the respective matching recess 4.

Figure 6:
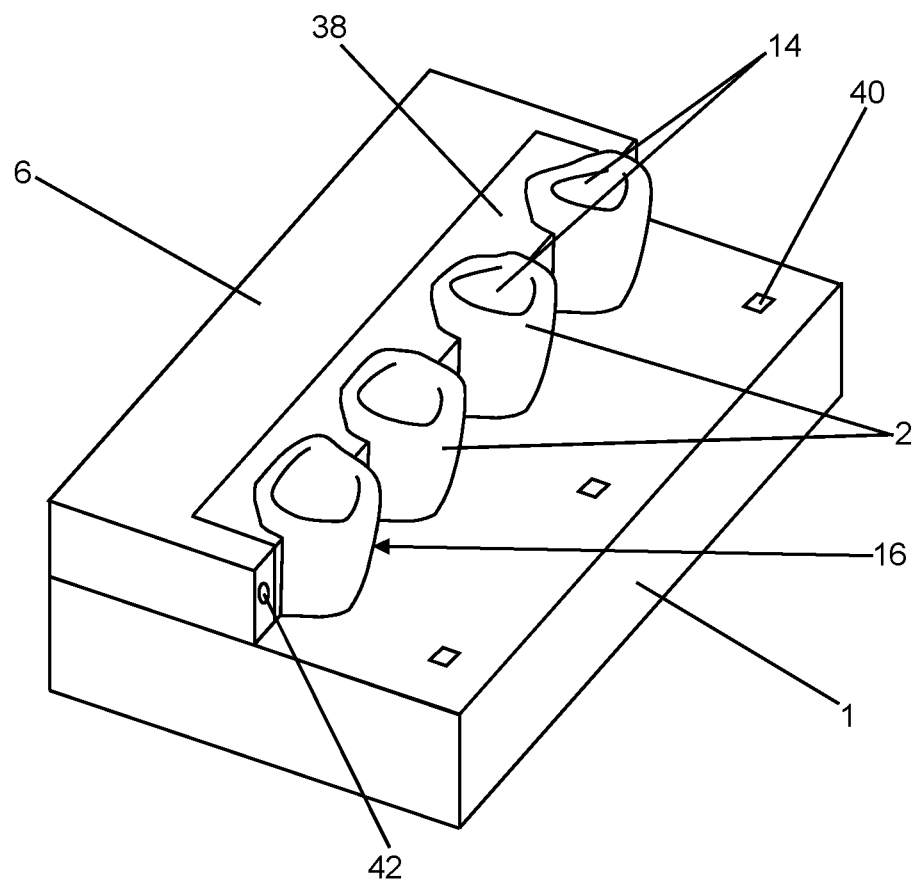
FIG. 6: shows a schematic perspective view onto the negative form shown in FIG. 5 and a first part of a clamping unit of a device according to the invention placed onto the prosthetic teeth.

Next, a first part of a clamping unit 6 with a synthetic insert 38 made of a material with a sufficiently high elasticity modulus (for example greater than 1 GPa) and with four semi-spherical recesses that roughly fit the outer forms of the tooth necks 16 of the prosthetic teeth 2 positioned in the negative form 1 is set down onto the negative form 1 and applied to the prosthetic teeth 2. FIG. 6 shows a schematic perspective view of the first part of the clamping unit 6 of a device according to the invention applied on the negative form 1 and to prosthetic teeth 2.

The clamping unit 6 is connected to the negative form 1 via three pins (not visible in FIGS. 4 to 7), which are inserted into the negative form 1 into the three left-hand grooves 40 (on the left-hand side in FIGS. 4 and 5). The pins are firmly connected to the underside of the clamping unit 6. The inner surfaces of the recesses in the synthetic insert 38 are smaller than the outer forms of the prosthetic teeth 2 in a middle area, which starts at a height of the prosthetic teeth 2, which protrudes from the recesses 4 of the negative form 1, i.e. on the tooth necks 16. Due to the smaller recesses in the synthetic insert 38 of the clamping unit 6 compared to the expansion of the prosthetic teeth 2 on the tooth necks 16, it is achieved that the synthetic insert 38 is compressed (as shown in FIG. 6) and as a result an elastic force is exerted onto the inserted prosthetic teeth 2.

The inner surfaces of the four recesses in the synthetic insert 38 and the form of the recesses 4 can be generated with a CAD/CAM method, whereby the forms used to produce the prosthetic teeth 2 are used as a data set or are previously read or scanned in. On the connecting surface to a second part of the clamping unit 6 (not visible in FIG. 6), click mechanisms 42 or latch connections 42 are provided, which match corresponding counterpieces on the connecting surface of the second part of the clamping unit 6. As a next method step, therefore, the second part of the clamping unit 6 is applied.

Figure 7:
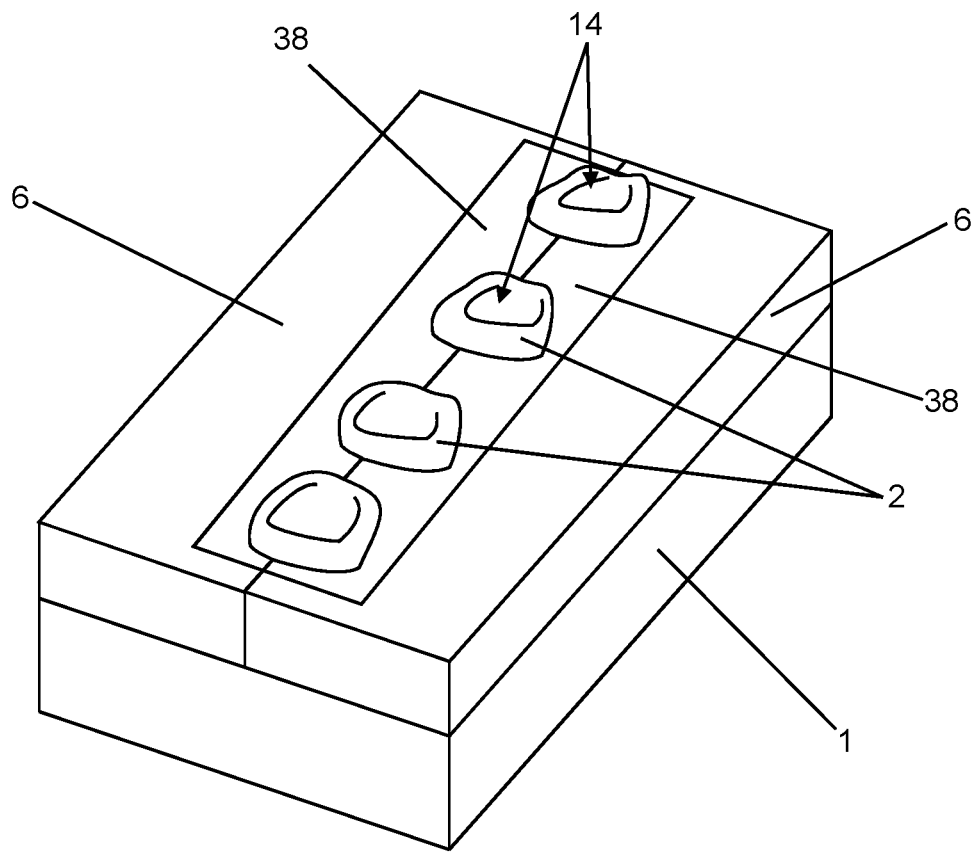
FIG. 7: shows a schematic perspective view onto the negative form shown in FIG. 5 with a complete clamping unit of a device according to the invention placed onto the prosthetic teeth.

FIG. 7 shows a schematic perspective view of the negative form 1 and the two-part clamping unit 6 of a device according to the invention applied to prosthetic teeth 2. The second part of the clamping unit 6 is, possibly aside from the recesses in the synthetic insert 38, designed as a mirror image of the first part of the clamping unit 6. The two parts of the clamping unit 6 are connected to each other via the click mechanisms 42 or latch connections 42. Without particular disadvantages, the clamping unit 6 could also be divided multiple times into a larger number of parts. For example, it would also be possible for each prosthetic teeth 2 to provide two parts respectively of the clamping unit 6, and to design the different parts in such a way that they can be connected to each other at the side. Such a system has the advantage that always only the desired prosthetic teeth 2 need to be tensioned. Such a system is a particularly variable further development of the present invention. The recesses of the synthetic insert 38 of the second part of the clamping unit 6 are applied on the negative form 1 on the prosthetic teeth 2. In precisely the same way as for the first part of the clamping unit 6, the second part has recesses in the synthetic insert 38 for the prosthetic teeth 2, which enclose the prosthetic teeth 2 in a middle area over half the side and lie flush there, so that the synthetic insert 38 is compressed and exerts an elastic force onto the prosthetic teeth 2.

The second part of the clamping unit 6 is also connected to the negative form 1 via three pins (not visible in FIGS. 4 to 7), which are inserted into the negative form 1 into the three right-hand grooves 40 (on the right-hand side in FIGS. 4 and 6). The pins are firmly connected to the underside of the clamping unit 6.

In theory, it is sufficient when only partial sections of the inner areas of the recesses of the synthetic insert 38 or another elastic holding means such as a metal brace 8 shown in FIG. 1 or a synthetic tensioner 28 shown in FIG. 2 in the clamping unit 6 are applied to the prosthetic teeth 2.

Preferably, in this case, the holding means 8, 28, 38 should press onto the prosthetic teeth 2 from at least three directions, so that they remain stably held and cannot turn about an axis on the plane of the holding means 8, 28, 38.

However, it is preferred according to the invention when the recesses of the synthetic insert 38 of the device are applied in full, flat and in a form-fit manner to the prosthetic teeth 2, since as a result, a stable hold of the prosthetic teeth 2 in the device is secured on the one hand, while on the other, the risk of a deformation or damage to the prosthetic teeth 2 by the clamping unit 6 can be avoided. The higher the elasticity modulus of the material for the clamping unit 6 can be selected, the more precisely the prosthetic teeth 2 are also positioned and oriented during processing.

After affixing the prosthetic teeth 2 in the middle area between the basal end 14 and the coronal end 12 of the prosthetic teeth 2 by means of the clamping unit 6, the device is inserted into a computer-controlled mill.

Figure 8:
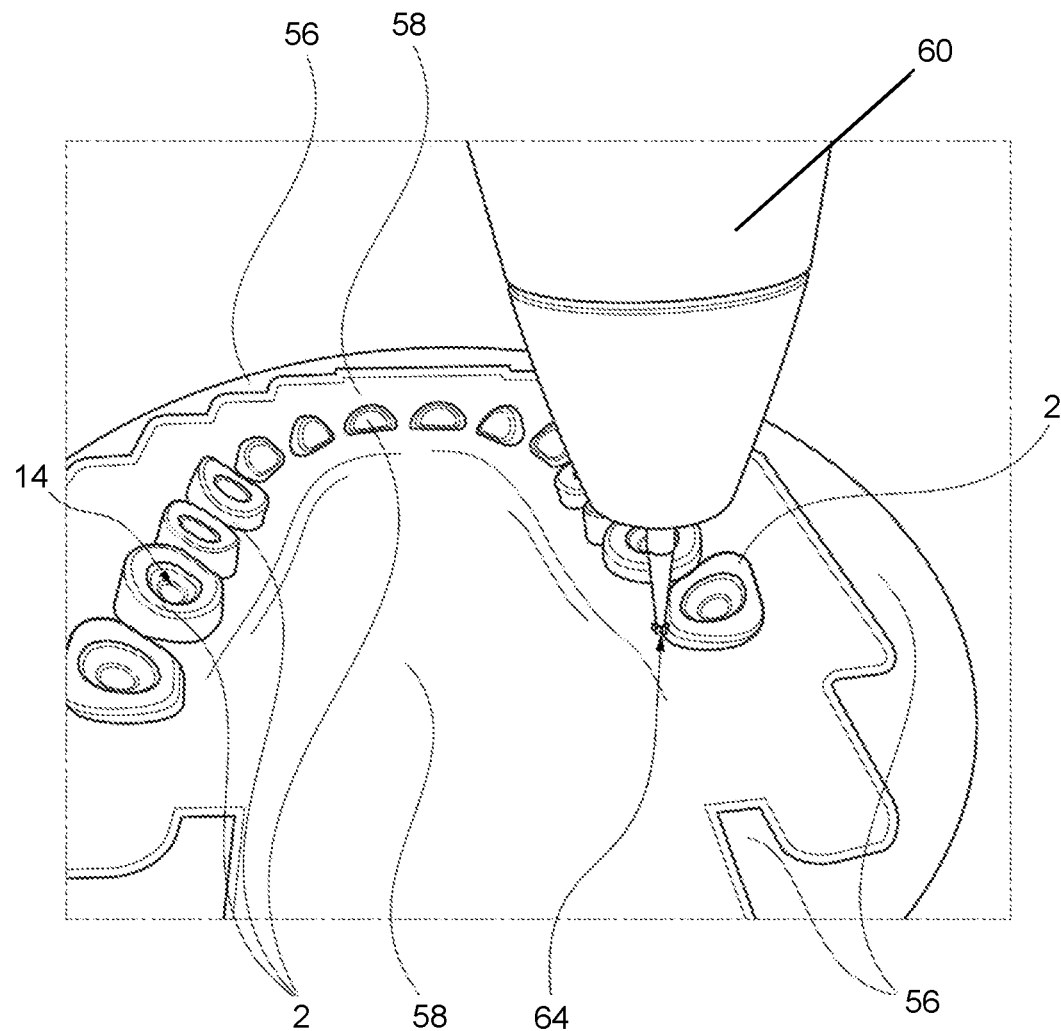
FIG. 8: shows a schematic perspective view onto a further device according to the invention, in which the prosthetic teeth are basally processed with a computer-controlled mill.

FIG. 8 shows a schematic perspective view onto a further device according to the invention, in which the prosthetic teeth 2 are processed on the basal side 14 with a computer-controlled mill 60. The device comprises a single-part clamping unit 56 and a negative form (not visible in FIG. 8), which is affixed on the underside of the clamping unit 56. In the interior of the clamping unit 56, there is a synthetic insert 58, which is placed or laid over the prosthetic teeth 2 positioned in recesses of the negative form. As a result, the prosthetic teeth 2 are pressed with their coronal side into the recesses of the negative form and affixed in the device. The device is tensioned into a mill holder of a computer-controlled mill 60 and milled fully automatically with a mill head 64. For this purpose, the known dimensions of the prosthetic teeth 2 and of the negative form relative to the holder of the mill 60 and the known positions of the prosthetic teeth 2 are made available to the computer as a data set for controlling the CAM method, i.e. for controlling the milling machine 60 or the mill head 64, and are taken into account in the calculation during control of the milling machine 60 or mill head 64.

The prosthetic teeth 2 can as a result be shorted on the basal sides 14 in a fully automated manner. Following the basal grinding of the prosthetic teeth 2, these can be removed from the device and glued into matching holders of a prosthetic base (not shown) in order to produce a finished set of teeth.

Alongside the data relating to the prosthetic teeth 2 and the device, the prosthetic teeth 2 can be processed on the basis of the data previously recorded in the mouth cavity of a patient in order to adapt the prosthetic teeth 2 to the mouth cavity situation. For a good seat, the prosthetic teeth 2 are basally processed for this purpose. Such methods are known, and for details, reference is made here to WO 2011/066 895 A1.

Following processing of the prosthetic teeth 2, the device is again removed from the milling machine 60 and the clamping unit 56 is separated from the negative form. The prosthetic teeth 2 are then provided individually and can be inserted into the prosthetic base.

The features of the invention disclosed in the above description, and in the claims, figures and exemplary embodiments, can be essential both individually and in any combination required for the realization of the invention in its different embodiments. Naturally, the device for the shown numbers of prosthetic teeth 2 and the shown exemplary embodiments with four and fourteen prosthetic teeth 2 can easily be transferred to other even and odd number quantities of prosthetic teeth 2, wherein the full set of twenty-eight prosthetic teeth 2 is preferred according to the invention.

LIST OF REFERENCE NUMERALS

1 Negative form
2 Prosthetic tooth
4 Recess as a negative of the coronal prosthetic tooth form
6 Clamping unit
8 Holding means/brace
10 Screw
12 Coronal side of the prosthetic tooth
14 Basal side of the prosthetic tooth
16 Tooth neck
18 Bore
20 Pin
28 Holding means/synthetic brace
38 Holding means/synthetic insert
40 Groove
42 Click mechanism/latch
56 Clamping unit
58 Holding means/synthetic insert
60 Computer-controlled milling machine
64 Mill head

The invention claimed is:

1. A device for holding prosthetic teeth (2), the device comprising a negative form and at least one clamping unit, wherein
recesses for holding coronal sides of the prosthetic teeth are provided in the negative form, wherein the recesses are formed in such a manner that the prosthetic teeth can be inserted in an unequivocal position and orientation into the recesses, wherein
the at least one clamping unit is affixable or is affixed to the negative form with a connecting means, and wherein the at least one clamping unit has at least one elastic holding means, wherein with the at least one elastic holding means, an elastic force is exercisable or is exerted from at least two different directions onto the prosthetic teeth inserted into the negative form, while the at least one clamping unit is affixed to the negative form, such that the prosthetic teeth are affixed in the device.

2. The device according to claim 1, wherein the at least one clamping unit is affixable on a side of the negative form in which the recesses are arranged.

3. The device according to claim 1, wherein the recesses form negatives of coronal ends of the prosthetic teeth.

4. The device according to claim 1, wherein the negative form has an even surface, in which the recesses are arranged.

5. The device according to claim 1, wherein the device has several prosthetic teeth, wherein the prosthetic teeth are inserted in the recesses and are affixed with the at least one clamping unit on the negative form.

6. The device according to claim 1, wherein the connecting means comprises at least one pin, at least one bore hole, at least one plug-in connection, at least one groove, at least one tongue, at least one bracket, at least one clamp, at least one threaded rod, at least one screw, at least one threaded bore, at least one latching means, at least one push button, or at least one adhesive, or a combination of these means, with which the at least one clamping unit is affixable or is affixed to the negative form.

7. The device according to claim 1, wherein the negative form is a single part.

8. The device according to claim 1, wherein the at least one clamping unit is multi-part, and on the parts of the at least one clamping unit, fastening means are provided via which the parts are to be affixed to each other.

9. The device according to claim 1, wherein the at least one elastic holding means is a non-plastically deformable material.

10. The device according to claim 1, wherein the at least one elastic holding means is at least one metal strip.

11. The device according to claim 1, wherein the basal ends of the prosthetic teeth affixed in the device protrude from the composite device.

12. The device according to claim 1, wherein the recesses are of such a depth that they extend up to a maximum of a beginning of undercut zones of the prosthetic teeth.

13. The device according to claim 1, wherein in each recess, at least one through-connection is provided, through which an underpressure is producible in the recess.

14. The device according to claim 1, wherein the at least one holding means of the at least one clamping unit is applied to tooth necks of the prosthetic teeth.

15. The device according to claim 1, wherein a sum of the elastic forces of the at least one holding means applied onto the prosthetic teeth presses the prosthetic teeth in a direction of the recesses of the negative form.

16. A method for affixing, and optionally for processing, prosthetic teeth with a device according to claim 1, the method having the following method steps:
inserting several prosthetic teeth into recesses of the negative form,
subsequently, applying at least one clamping unit to the inserted prosthetic teeth, wherein the at least one elastic holding means of the at least one clamping unit is applied on at least two directions on tooth necks of the prosthetic teeth, and
affixing the at least one clamping unit on the negative form, so that an elastic force of the at least one elastic holding means acts on the prosthetic teeth from at least two directions, wherein the prosthetic teeth are affixed against the negative form as a result.

17. The method according to claim 16, wherein when the at least one clamping unit is applied, the at least one holding means encloses the prosthetic teeth on their tooth necks at least in sections, wherein inner areas of the at least one holding means fit at least in sections in an engaging manner to sections of outer areas of the prosthetic teeth.

18. The method according to claim 16, comprising applying the at least one clamping unit to the prosthetic teeth in such a manner that basal ends of the prosthetic teeth protrude.

19. The method according to claim 16, comprising affixing the at least one clamping unit and the negative form with the prosthetic teeth affixed in it in a defined position in a holder of a CAM device for removing material of the prosthetic teeth with a CAM method, and processing at least one basal end of at least one prosthetic tooth in a computer-controlled manner using the CAM device.

20. The method according to claim 16, wherein outer forms of all pre-fabricated prosthetic teeth used are present as a first data set, and a second data set defines precise positions of all affixed pre-fabricated prosthetic teeth in the negative form, comprising conducting a subsequent processing at least of one prosthetic tooth on the basis of the first and second data set.

21. The method according to claim 16, wherein all pre-fabricated prosthetic teeth can only be inserted in one specified position and orientation respectively into the negative form, and can be affixed with the at least one clamping unit.

22. The method according to claim 16, comprising before inserting the prosthetic teeth into the negative form, applying a bonding agent to a surface of the recesses and/or to a surface of coronal sides of the prosthetic teeth.

23. A set for implementing a method for affixing, and optionally for processing, prosthetic teeth, the set having several pre-fabricated prosthetic teeth and at least one device according to claim 1.

24. The set according to claim 23, wherein the set additionally contains a first data set on an outer form of all pre-fabricated prosthetic teeth, and a second data set on a position of the pre-fabricated prosthetic teeth in a composite device.

25. The device according to claim 4, wherein the negative form has a standing side or arrangement area opposite the even surface.

26. The device according to claim 25, wherein the negative form is a plate.

27. The device according to claim 9, wherein the at least one elastic holding means is a non-plastically deformable material with an elasticity modulus of at least 0.2 GPa.

28. The device according to claim 27, wherein the at least one elastic holding means is a non-plastically deformable material with an elasticity modulus of 0.2 GPa to 6 GPa.

29. The device according to claim 10, wherein the at least one elastic holding means is at least one strip made of spring steel.

30. The device according to claim 29, wherein synthetic coatings are provided on the surfaces of the holding means pointing towards the prosthetic teeth.

31. The method according to claim 19, wherein the CAM device is a computer-controlled milling machine.

32. The method according to claim 31, wherein the CAM device is a computer-controlled four-axis mill or five-axis mill.

33. The method according to claim 20, wherein outer forms of all prefabricated prosthetic teeth used are present as a first data set, and a second data set defines precise positions of all affixed pre-fabricated prosthetic teeth in the negative form, comprising conducting a subsequent processing at least of one prosthetic tooth on the basis of the first and second data set using a CAD/CAM method.

34. The set according to claim 24, wherein the set additionally contains a first data set on an outer form of all pre-fabricated prosthetic teeth, and a second data set on a position of the pre-fabricated prosthetic teeth on a data storage device.

* * * * *